US007926943B1

(12) United States Patent
Reichow et al.

(10) Patent No.: US 7,926,943 B1
(45) Date of Patent: Apr. 19, 2011

(54) PERIPHERAL VISION TRAINING AND/OR TESTING DURING CENTRAL VISION FIXATION

(75) Inventors: Alan W. Reichow, Beaverton, OR (US); Herb Yoo, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 12/615,349

(22) Filed: Nov. 10, 2009

(51) Int. Cl.
*A61B 3/02* (2006.01)
(52) U.S. Cl. .................................. 351/203; 351/246
(58) Field of Classification Search .............. 351/203, 351/200, 205, 246, 247
See application file for complete search history.

(56) References Cited

U.S. PATENT DOCUMENTS

| | | | |
|---|---|---|---|
| 3,861,790 A | 1/1975 | Tamura | |
| 5,050,982 A | 9/1991 | Meissner | |
| 5,478,239 A | 12/1995 | Fuerst | |
| 6,755,525 B2 | 6/2004 | Reichow | |
| 6,811,258 B1 | 11/2004 | Grant | |
| 6,893,127 B2 | 5/2005 | Reichow | |
| 7,073,208 B2 | 7/2006 | Penque, Jr. et al. | |
| 7,699,466 B2 * | 4/2010 | Hayakawa et al. | 351/203 |

OTHER PUBLICATIONS

Reichow, et al, "Introduction to Behavioral Optometry", Sports Vision, 1993, 75 pages, Optometric Extension Program Foundation, United States.
Ferreira, "An Overview of Research in Sports Vision: its History and an Optometric Perspective", The South African Optometrist, Dec. 2003, pp. 142-149, vol. 62, No. 4, Auckland Park, South Africa.
Coffey, et al., "Visual Performance Enhancement in Sports Optometry", Sports Vision 1995, pp. 158-177, Butterworth-Heinermann, United States.
Cardall, "Contact Lenses in Sport: a General Overview", Optician, Jan. 13, 2006, pp. 22-25, vol. 231, No. 6034, United States.
Rouse, et al., "A Comparison Study of Dynamic Visual Acuity Between Athletes and Nonathletes", Journal of the American Optometric Association, Dec. 1988, pp. 946-950, vol. 59, No. 12, United States.
Koenig, "Practicing Perception: Eyes Can Be Trained to be More Effective", USA Today Baseball Weekly, 1996, 3 pages, United States.
Coffey, et al., "Optometric Evaluation of the Elite Athlete," Problems in Optometry, Mar. 1990, pp. 32-59, vol. 2, No. 1, United States.

(Continued)

*Primary Examiner* — Hung X Dang
(74) *Attorney, Agent, or Firm* — Shook, Hardy & Bacon L.L.P.

(57) ABSTRACT

Systems and methods may test and/or train the peripheral visual abilities of an individual. Peripheral visual abilities may be tested and/or trained while maintaining a central visual focus by the individual. A central display element may display central visual indicia, while a peripheral display element may display peripheral visual indicia. Each visual indicia displayed may possess one or more trait and, optionally, one or more property. Inputs may be received at a central input device and/or a peripheral input device, with inputs corresponding to the traits perceived to be possessed by displayed indicia. By determining the correspondence of received inputs to the traits possessed by corresponding indicia, the peripheral visual abilities of an individual may be tested and/or trained in accordance with the present invention.

18 Claims, 9 Drawing Sheets

OTHER PUBLICATIONS

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 215-325, vol. 16, No. 4, Begell House, Inc., United States.

International Search Report and Written Opinion for International Application PCT/US2010/55670, 6 pages.

* cited by examiner

PERIPHERAL VISION TRAINING AND/OR TESTING DURING CENTRAL VISION FIXATION

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates to training and/or testing the visual abilities of an individual. More particularly, the present invention relates to training and/or testing the peripheral vision of an individual, particularly the peripheral vision of an individual during central visual fixation.

BACKGROUND OF THE INVENTION

Visual abilities are critical to the success of individuals performing a wide variety of activities. In particular, many sporting activities place high demands upon the visual abilities of individual participants. In an otherwise closely matched sporting contest, the superior visual abilities of one competitor or team may be the crucial factor that determines which side wins the contest. A relatively easy to measure typical vision test, however, evaluates visual skills such as central visual clarity. Similarly, a typical remediation of a visual challenge identified in a typical vision test may utilize corrective lenses to improve the central visual clarity of an individual. Many of the visual abilities necessary for success in sports extend well beyond central visual clarity. For example, visual abilities such as peripheral vision can be critical to success in activities such as sports.

BRIEF SUMMARY OF THE INVENTION

The present invention provides systems and methods for training and/or testing the peripheral visual abilities of an individual. The present invention may further test and/or train the peripheral visual abilities of an individual while the individual is maintaining a central visual focus. The present invention may utilize a central visual display element that displays central visual indicia within the central field of view of an individual. The present invention may further utilize one or more peripheral display elements to display peripheral visual indicia in the peripheral fields of view of an individual. The central display element and peripheral display element may comprise a single display device or multiple display devices. The central visual indicia displayed on the central visual display element and the peripheral visual indicia displayed on the peripheral display elements may be the same type of visual indicia or different types of visual indicia. Visual indicia displayed on the central display element and/or peripheral display element may possess visual traits. A response to a displayed visual indicia may be made by an individual based upon the visual trait perceived by the individual to be possessed by that displayed visual indicia. Such an input may be made using an input device. Further, a displayed visual indicia may possess one or more properties. A property may comprise, for example, the position on a display element where a visual indicia was displayed, the brightness or color of a visual indicia, or other properties that may impact the ability of an individual to perceive a displayed visual indicia and any trait that indicia may possess. By utilizing visual indicia having a variety of properties, the peripheral visual skills of an individual may be trained and/or tested under a variety of conditions and circumstances, such that any potential areas of peripheral visual improvement may be readily identified and/or trained.

BRIEF DESCRIPTION OF THE SEVERAL VIEWS OF THE DRAWING

The present invention is described in detail below with reference to the attached drawing figures, wherein.

DETAILED DESCRIPTION OF THE INVENTION

Figure 1:
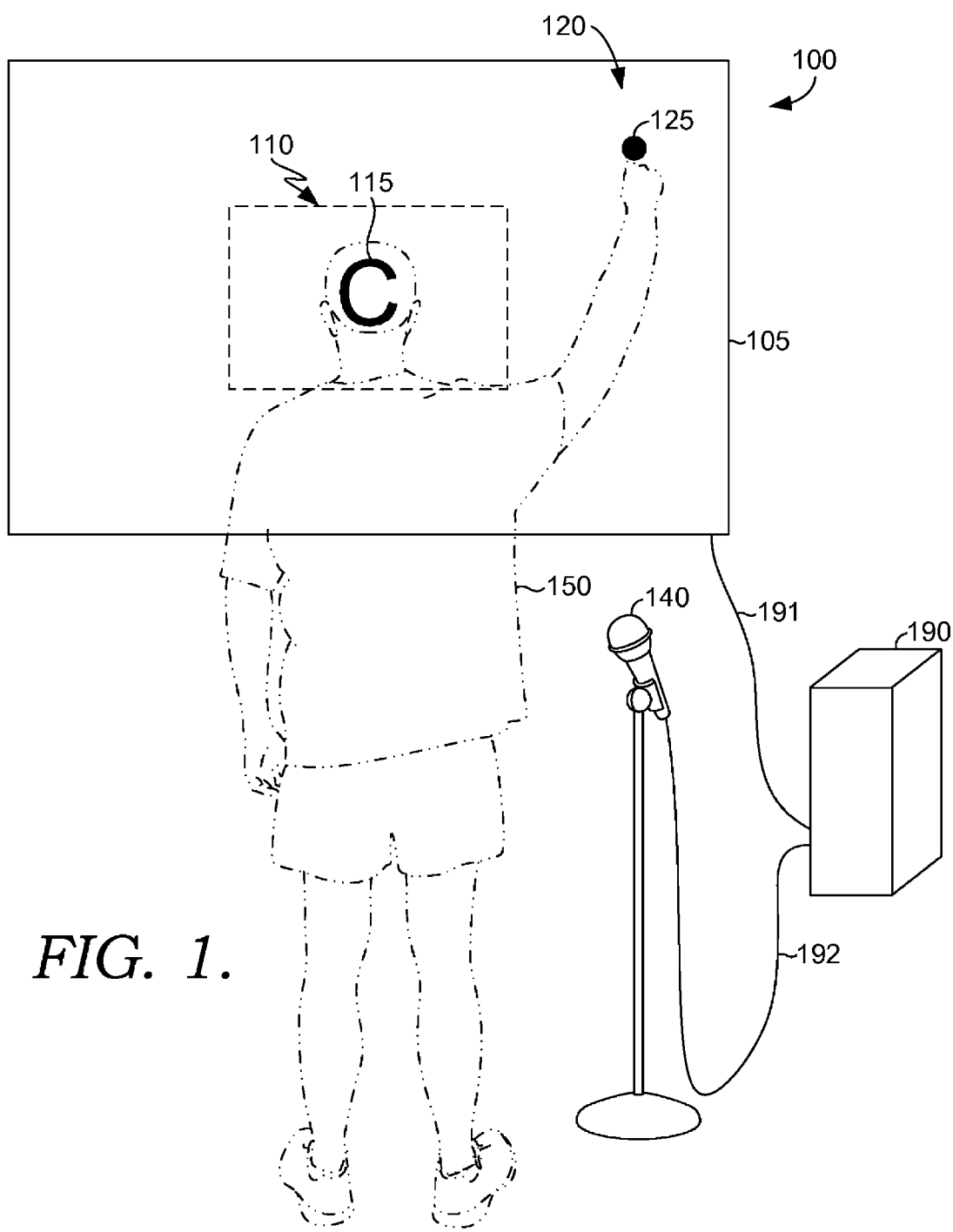
FIG. 1 illustrates a system for training and/or testing the peripheral visual abilities of an individual.

Referring now to FIG. 1, a system 100 for training and/or testing the peripheral visual abilities of an individual 150 is illustrated. System 100 may comprise a central display element 110 and a peripheral display element 120. Central display element 110 and peripheral display element 120 may comprise portions of a larger display device 105. In the example illustrated in FIG. 1, display device 105 may comprise a touch-sensitive monitor. As illustrated in the example of FIG. 1, individual 150 may register an input using display device 105 as a touch-sensitive input device for responding to peripheral visual indicia such as indicia 125 displayed in the peripheral display element 120. In the example illustrated in FIG. 1, central display element 110 displays a central visual indicia 115. Central visual indicia 115 in this example comprises a Landolt C possessing a trait of orientation, in this example to the right. Individual 150 may respond to central visual indicia 115 and the trait it possesses using central input device 140, in this example a microphone. For example, individual 150 may verbally say "right" in response to the displayed central visual indicia 115 to indicate that individual 150 perceived the displayed central visual indicia 115 and the trait it possessed. Microphone 140 may operate in conjunction with appropriate voice recognition software operating on control unit 190. Control unit 190 may be connected to microphone 140 via connection 192 and may be connected to display device 105 via connection 191. Control unit 190 may comprise any type of computing device to control the display of visual indicia and the receipt of inputs such as, in the present example, the receipt of verbal inputs from individual 150 via microphone 140 and the display of visual indicia on display device 105 in central display element 110 and peripheral display element 120. In the present example, control unit 190 may further operate to receive inputs in the form of physical touches from touch-sensitive display device 105 and to compare inputs received with the traits possessed by displayed visual indicia to determine whether individual 150 correctly perceived the trait possessed by a displayed indicia.

Still referring to FIG. 1, a peripheral visual indicia 125 may comprise a dot or other activated region of peripheral display element 120. In the present example, peripheral visual indicia 125 possesses the trait of location, which may be defined as a coordinate position on display device 105 or in terms of its displayed location relative to individual 150. Individual 150 may respond to peripheral visual indicia 125 and its location by physically touching the surface of display device 105 at the location of the displayed peripheral visual indicia.

While FIG. 1 illustrates a specific example of a system 100 in accordance with the present invention, other variations are possible. A few examples of other possible embodiments of the present invention are described below, but they are by no means exhaustive of the possibilities for training and/or testing the peripheral visual abilities of an individual in accordance with the present invention.

Figure 2:
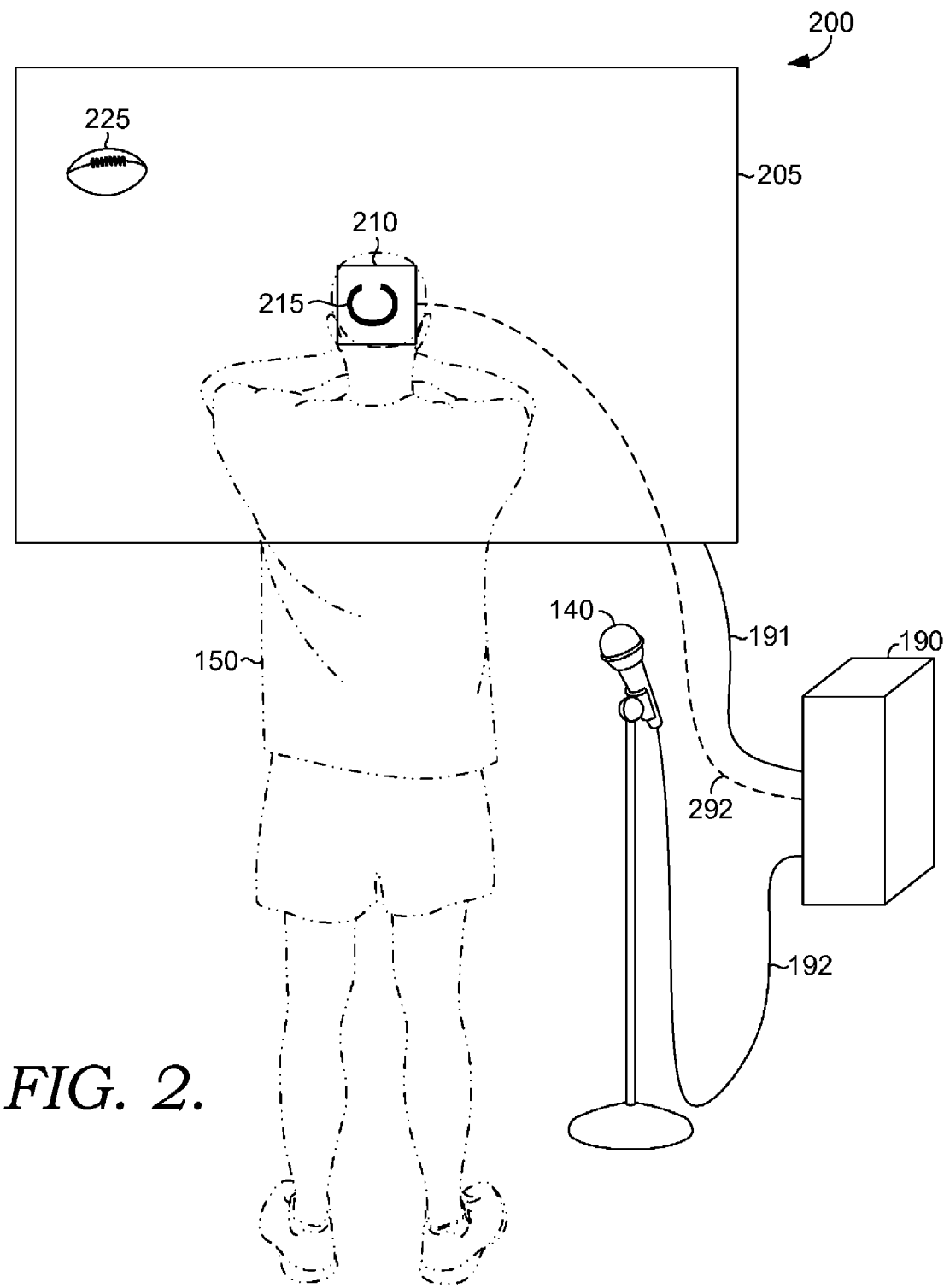
FIG. 2 illustrates a further system for training and/or testing the peripheral visual abilities of an individual.

Referring now to FIG. 2, a further system 200 in accordance with the present invention is illustrated. In the example illustrated in FIG. 2, central display device and central input device may comprise a single multi-touch device 210 held in the hand of individual 150. In the example illustrated in FIG. 2, multi-touch device displays a Landolt C possessing a trait of orientation, in this example upwards. Individual 150 may respond to central visual indicia 215 by stroking multi-touch device upwards to indicate that individual 150 perceived central visual indicia 215 and the trait it possessed. Multi-touch device 210 may communicate with control unit 190 via wireless connection 292, which may utilize any wireless protocol, such as various 802.11 protocols, Bluetooth, or other wireless communication protocols. Peripheral display element in the example illustrated in FIG. 2 may comprise the entirety of display device 205. Peripheral visual element 225 may possess a trait of identity, in this example in American football. Individual 150 may respond to peripheral visual indicia 225 by verbally stating the identity of the indicia, in this case "football" such that microphone 140, now operating as a peripheral input device, may receive the response from individual 150 and operating in conjunction with control unit 190 via connection 192, receive and optionally analyze the response from individual 150 to determine whether individual 150 correctly perceived peripheral visual indicia 225 and the trait that indicia possessed. In the example illustrated in FIG. 2, peripheral visual indicia 225 possesses the trait of identity, in this example an American football, as well as a property that does not determine the appropriate response by individual 150 but that may be useful in analyzing the training and/or testing performance of individual. In the present example illustrated in FIG. 2, the property possessed by peripheral visual indicia may, for example, be its location on display device 205. For example, peripheral visual ability testing using system 200 may identify that individual 150 encounters more difficulty correctly perceiving displayed peripheral visual indicia in the upper left quadrant of display device 205. Thereafter, training of the peripheral visual abilities of individual 150 may particularly be directed to improving the peripheral visual abilities of individual 150 using peripheral visual indicia possessing the trait of being positioned in the upper left-hand quadrant of display device 205 to improve the abilities of individual 150.

Figure 3:
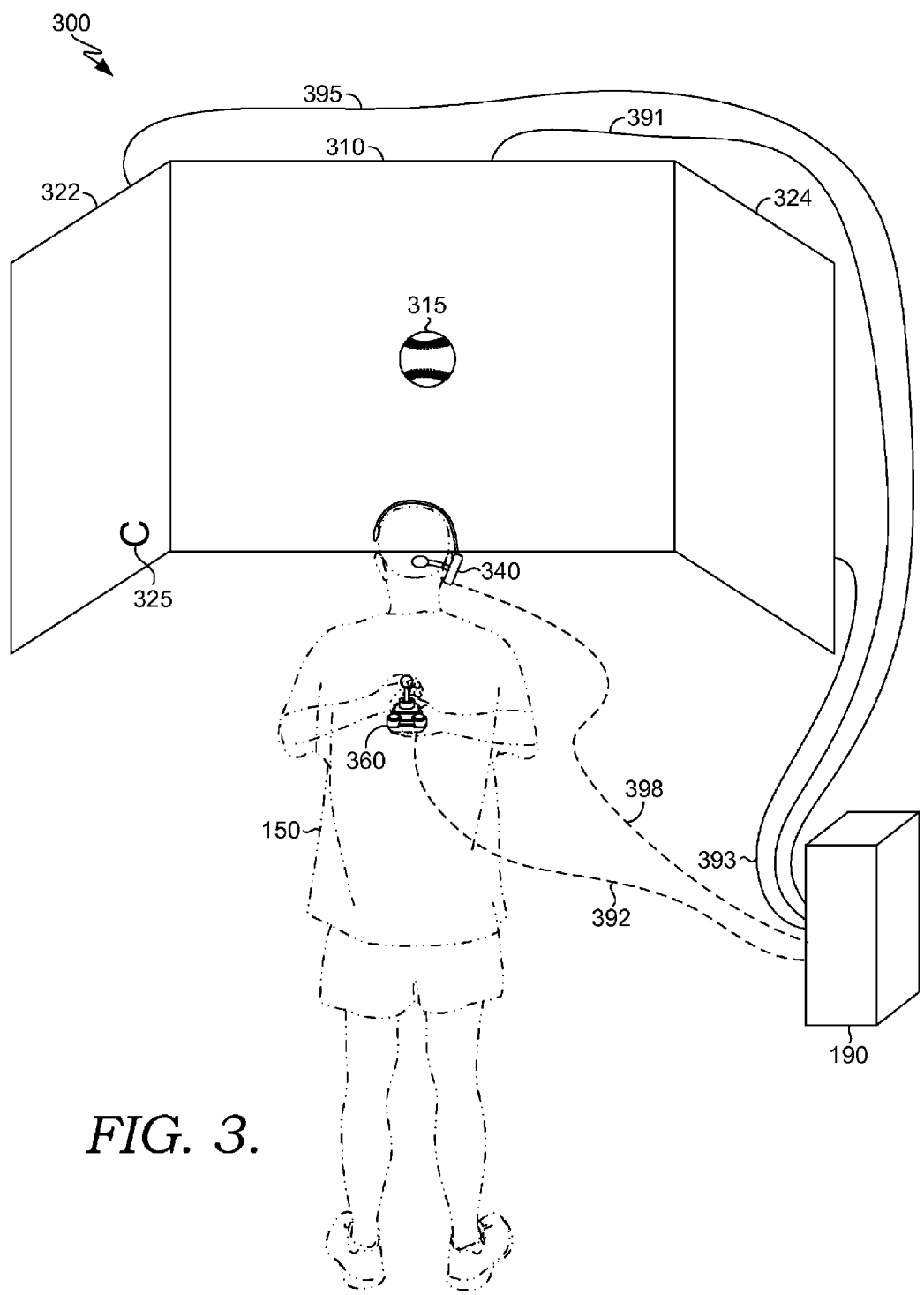
FIG. 3 illustrates a further system for training and/or testing the peripheral visual abilities of an individual.

Referring now to FIG. 3, a further system 300 for training and/or testing the peripheral visual abilities of an individual 150 is illustrated. In the example illustrated in FIG. 3, peripheral display element may comprise a left display device 322 and a right display device 324, while central display element may comprise a central display device 310. Control unit 190 may operate to control the display of visual indicia on left peripheral display element 322 via connection 395 and to control the display of visual indicia on right peripheral display element 324 via connection 393. Similarly, control unit 190 may operate to control the display of visual indicia on central display element 310 via connection 391. In the example illustrated in FIG. 3, a central visual indicia 315 may possess a trait, in this example the trait of identity as a baseball. Individual 350 may respond to the displayed central visual indicia 315 by verbally identifying the indicia 315 by saying "baseball." In the example of FIG. 3, central input device may comprise a headset and microphone 340 in wireless communication with control unit 190 via link 398. As in the above examples, microphone 340 may operate in conjunction with appropriate software operating on control unit 190 to receive and/or analyze the verbal response of subject 150. Peripheral display element, in this example left peripheral display element 322, may display a peripheral visual indicia 325 possessing a trait, in this example an upward orientation. Individual 150 may respond to the perceived trait using a peripheral input device, in the example joy stick 360 wireless communication with control unit 190 via wireless link 392. In the example illustrated in FIG. 3, peripheral visual indicia 325 may also possess visual properties, such as its location relative to individual 150, and these and other visual properties may be utilized, for example by control unit 190, in the training and/or testing of the peripheral visual abilities of individual 150.

Figure 4:
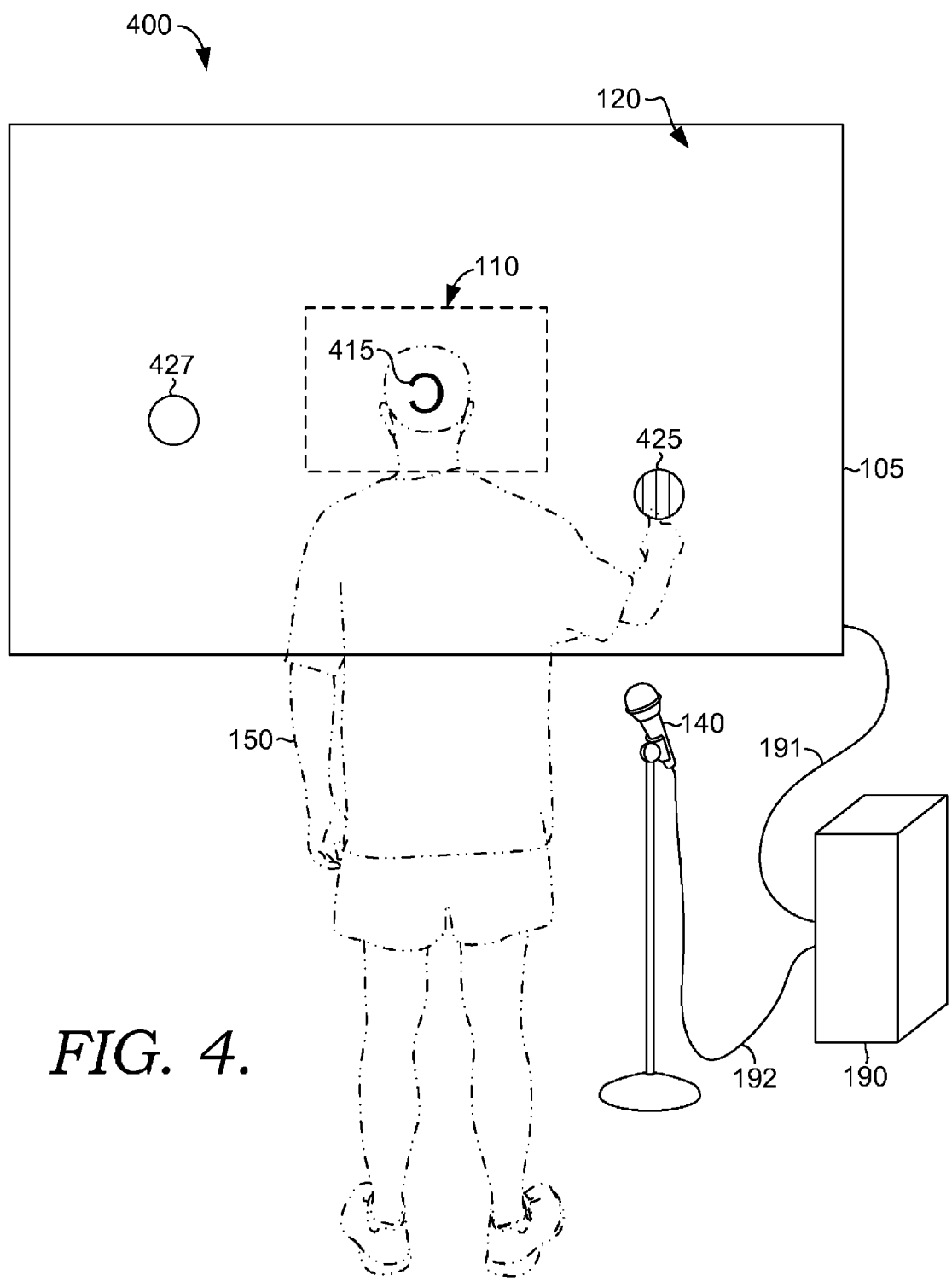
FIG. 4 illustrates a further system for training and/or testing the peripheral visual abilities of an individual.

Referring now to FIG. 4, a further system 400 in accordance with the present invention for training and/or testing the peripheral visual abilities of an individual 150 is illustrated. A single touch-sensitive display device 105 may comprise a central display element 110, a peripheral display element 120, and a peripheral input device. A central visual indicia 415 may comprise a Landolt C possessing the trait of orientation, in the example illustrated in FIG. 4 an orientation to the left. Individual 150 may respond to central visual indicia 415 and the trait individual 150 perceives the indicia as possessing verbally by stating "left" using microphone 140 and associated voice-recognition software operating upon control unit 190. Peripheral display element 120 may display peripheral visual indicia possessing a variety of traits. For example, a first peripheral visual indicia 425 may possess a particular physical location on display device 105 relative to individual 150, in this instance to the right of individual 150, and may further possess a trait of color, as indicated by the shading of indicia 425 in FIG. 4. A second peripheral visual indicia 427 may possess differing traits from the first peripheral visual indicia 425, in the present example a different position on display device 105 relative to individual 150 and the absence of coloration. In accordance with the present invention, individual 150 may selectively respond to a plurality of displayed peripheral visual indicia based upon the trait or traits possessed by each displayed peripheral visual indicia. For example, as illustrated in FIG. 4 individual 150 has responded to first peripheral visual indicia 425 by physically touching display device 105 at the location of display of first peripheral visual indicia 425, but has not responded to second peripheral visual indicia 427. The response of individual 150 may be based upon any trait possessed by a visual indicia, such as color, identity, position, or the like. Both correct and incorrect responses may be recorded and analyzed by control unit 190. Further, a plurality of indicia possessing one or more traits may be displayed as central visual indicia in a central display element 110, although such a variation is not illustrated in the present example.

Figure 5:
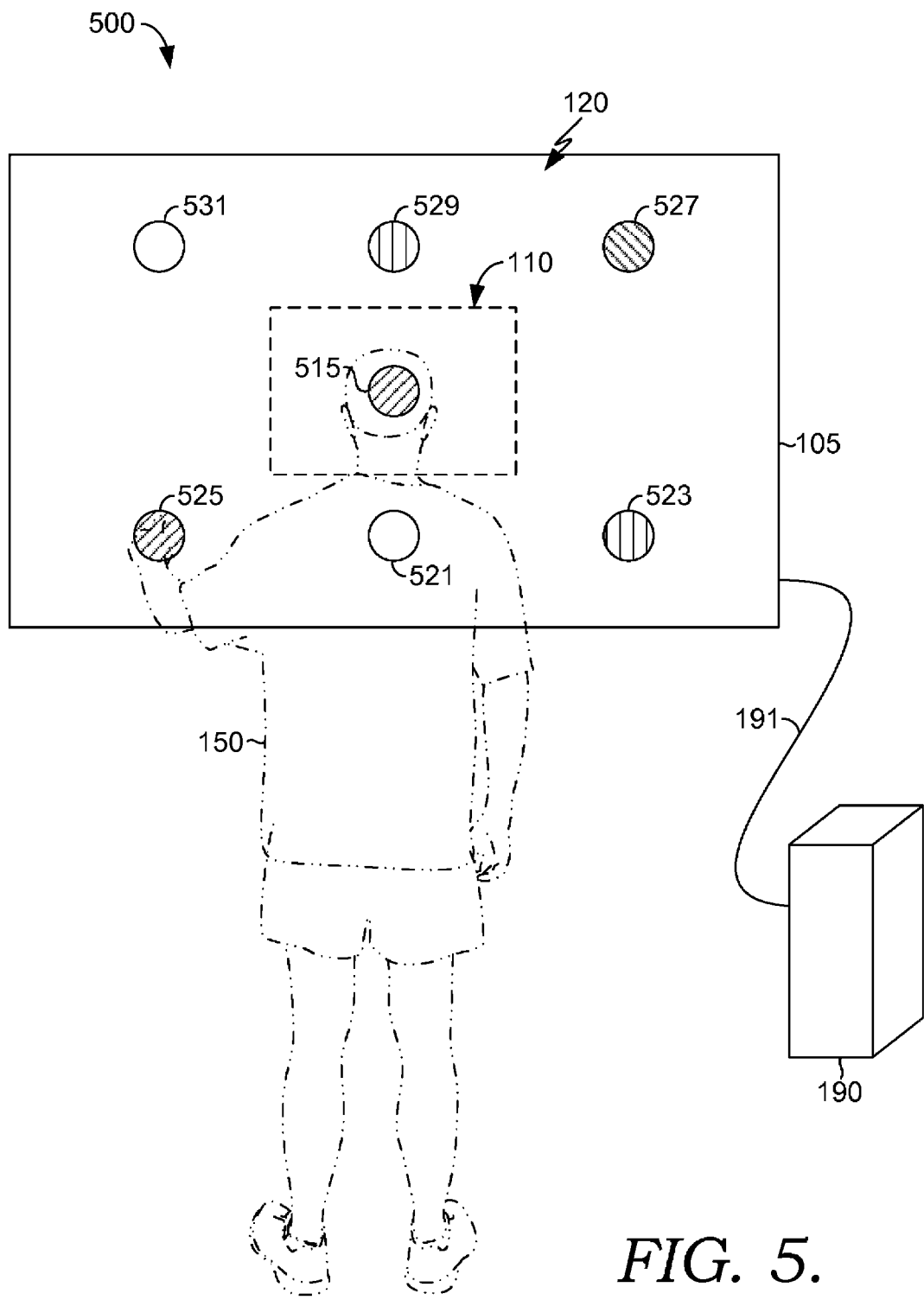
FIG. 5 illustrates a further system for training and/or testing the peripheral visual abilities of an individual.

Referring now to FIG. 5, a further system 500 for training and/or testing the peripheral visual abilities of an individual 150 is illustrated. System 500 may comprise a single display device 105 having a central display element 110 and a peripheral display element 120. The display of visual indicia on display device within central display element 110 and peripheral display element 120 may be controlled by control unit 190 via connection 191. Display device may comprise a touch-sensitive monitor, such that inputs may be registered by individual through touching the surface of display device 150. In the example illustrated in FIG. 5, a central visual indicia 515 may be displayed in central display element 110. Central visual indicia 515 may possess a particular trait, in the example illustrated the trait of coloration as indicated by shading illustrating a first coloration. A plurality of peripheral visual indicia may be displayed in peripheral display element 120. Each of the plurality of peripheral visual indicia may possess one or more traits, such as coloration as indicated by shading in the present example. In the example illustrated in FIG. 5, the plurality of peripheral visual indicia comprises a first peripheral visual indicia 521 and a second peripheral visual indicia 531 possessing a second coloration, a third peripheral visual indicia 523 and a fourth peripheral visual indicia 529 both possessing a third color, a fifth peripheral visual indicia 527 possessing yet a fourth color, and finally a matching peripheral visual indicia 525 that possesses the same trait, in this example a first coloration, as central visual indicia 515. As illustrated in the example of FIG. 5, individual 550 selects matching peripheral visual indicia 525 by contacting display device 105 at the position occupied by matching peripheral visual indicia 525. The plurality of peripheral visual indicia may be displayed commencing at different times and at a variety of locations on peripheral display element 120, but may also be displayed commencing and ending at the same times. Of course, traits other than or in addition to color may be shared between a central visual indicia and a matching peripheral visual indicia. For example, identity, orientation, visual pattern, or any other visual trait may be shared by a central visual indicia and a matching peripheral visual indicia. Further, more than a single trait may be required to be shared by a central visual indicia and a peripheral visual indicia in order for the peripheral visual indicia to comprise a matching peripheral visual indicia. By way of yet further example, a peripheral visual indicia may be displayed possessing one or more visual trait that may be used to determine which of a plurality of central visual indicia, comprise a matching central visual indicia.

Figure 6:
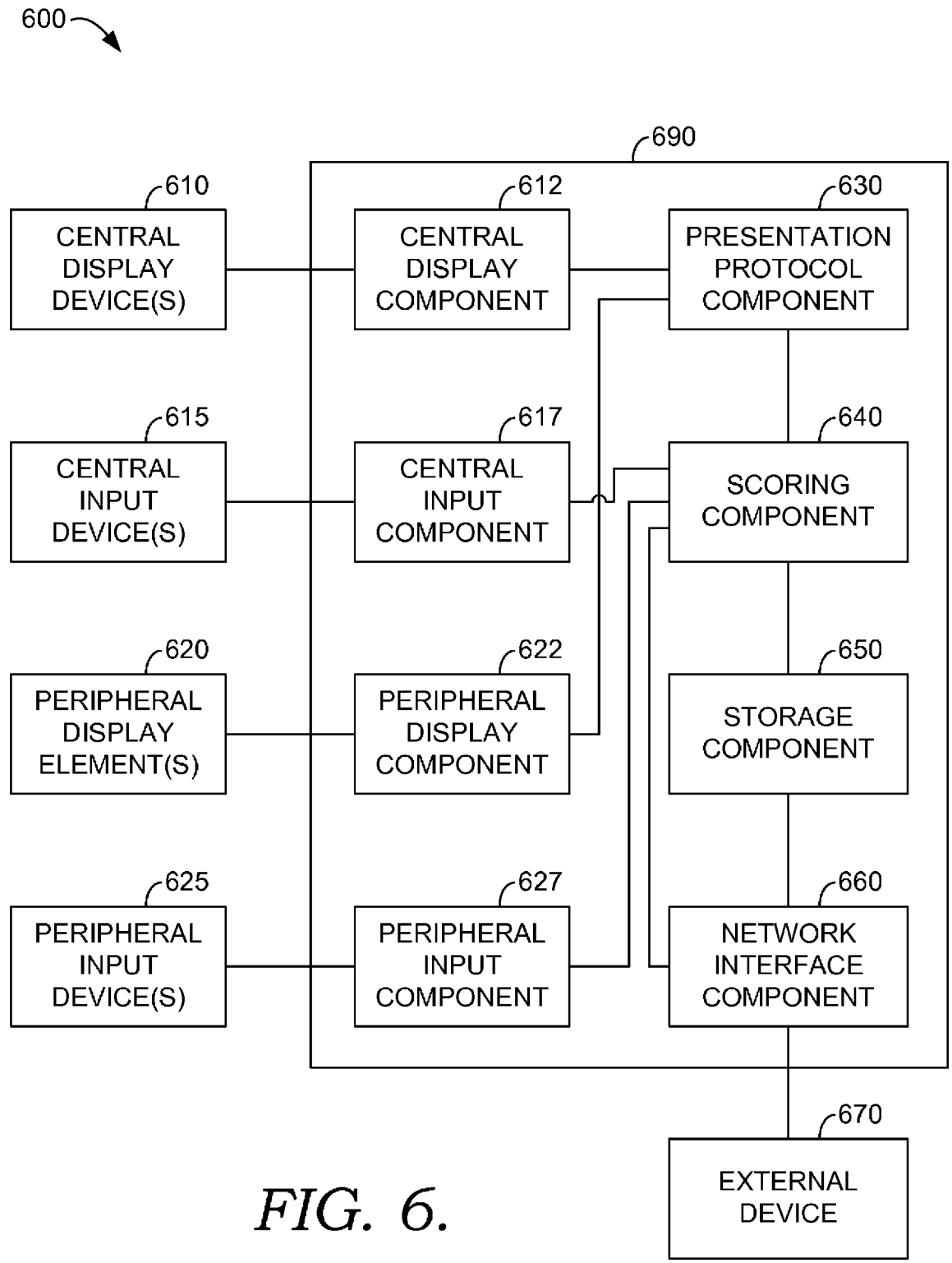
FIG. 6 illustrates a computing system for use in training and/or testing the peripheral visual abilities of an individual.

Referring now to FIG. 6, a computing environment for 600 for use in conjunction with systems and methods for training and/or testing the peripheral visual abilities of an individual is illustrated. Environment 600 may comprise a control unit 690 having a variety of operational components. The various components of control unit 690 may comprise appropriate software to cause processing units, memory components, input/output interfaces, and other types of equipment to perform in accordance with the methods of the present invention. Control unit 690 may interface with a central display element 610, a central input device 615, a peripheral display element 620, and a peripheral input device 625. Of course, these elements may be omitted or combined in ways such as those described above. For example, central display element 610 and peripheral display element 620 may comprise a single display device, for example as illustrated in FIG. 1. Control unit 690 may operate to control the display of indicia on display devices and to receive inputs from input devices. Control unit 690 may comprise a central display component 612 that interfaces with central display element 610 to control the display of central visual indicia. The central display component 612 may control the traits, properties, duration, and the like involved in the display of a central visual indicia. Peripheral display component 622 may likewise interface with a peripheral display element 620 and may control the display of peripheral visual indicia, such as controlling the traits, properties, duration of display, and the like of peripheral display indicia. In an instance where central display element 610 and peripheral display element 620 comprise different portions of a single display device, central display component 612 and peripheral display component 622 may optionally be combined in to a single component, or may comprise different aspects of a single component.

Central input device 615 may interface with central input component 617, to permit inputs from an individual identifying perceived traits possessed by central display indicia to be entered by an individual at central input device 615 and transmitted to control unit 690. Similarly, peripheral input device 625 may interface with peripheral input component 627 to receive inputs from an individual by identifying the traits possessed by peripheral visual indicia as perceived by an individual. Central input device 615 and/or peripheral input device 625 may comprise a touch-sensitive screen, microphones, joy sticks, or any other mechanism whereby an individual may register an input identifying a trait the individual believes is possessed by a displayed visual indicia. Further, a single input device may be used in some circumstances, such as when, as illustrated in the example of FIG. 5, the identify of a trait possessed by one type of indicia, either central or peripheral, determines the appropriate response to the other kind of indicia.

A presentation protocol component 630 may determine what central visual indicia to display on a central display element via central display component and what type of peripheral visual indicia to display on peripheral element 620 via peripheral display component 622. Presentation component 630 may interface with a scoring component 640 to adjust the types and difficulty of indicia displayed via central display component 612 and peripheral display component 622. Scoring component 640 may interface with central input component 617 to receive inputs entered at central input device 615, and may further interface with peripheral input component 627 to receive peripheral inputs from peripheral input device 625. Scoring component 640 may compare received inputs to the indicia types displayed at the control of presentation protocol component 630 to determine whether a given input correctly identifies a trait or traits possessed by a displayed visual indicia. Storage component 650 may interface with scoring component to receive and, if desired, store a score or basic presentation and/or input information regarding the display of visual indicia in the receipt of inputs. Network interface component 660 may interface with storage component and/or scoring component 640 to provide information to an external device 670. External device 670 may be an external server, an external storage device, a printer, an external monitor or other display device to provide scoring information or other data to a trainer, an eye care practitioner, or the individual undergoing testing and/or training. External device 670 may be accessed by network interface component 660 both to transmit and to retrieve data from external device 670. Network interface component 660 may access external device 670 via a direct connection, either wired or wireless, or over a network with any number of intervening devices.

Figure 7:
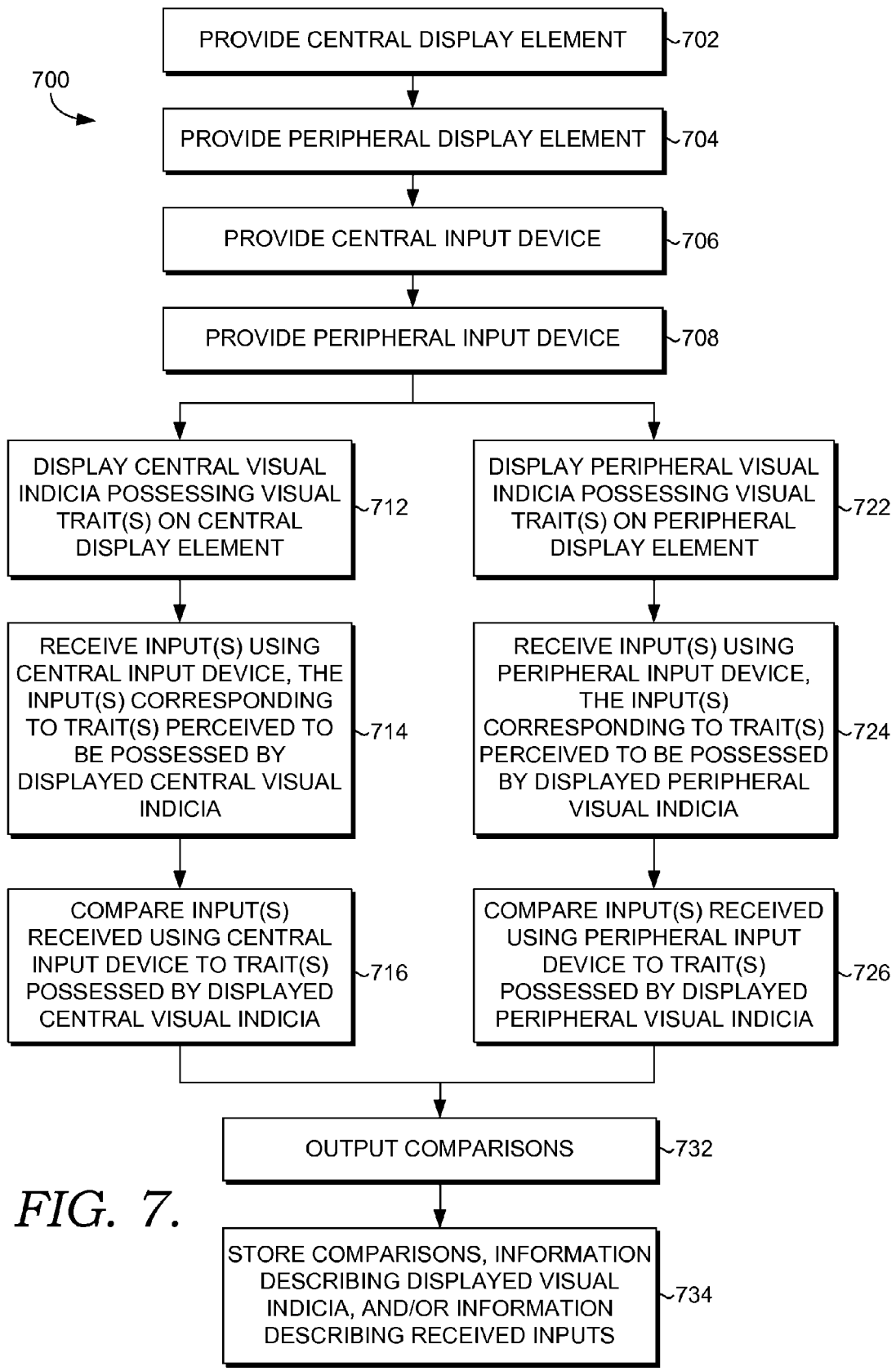
FIG. 7 illustrates a method for training and/or testing the peripheral visual abilities of an individual.

Referring now to FIG. 7, a method 700 for training and/or testing the peripheral visual abilities of an individual is illustrated. In step 702, a central display element viewable by the individual may be provided. In step 704, a peripheral display element viewable by the individual may be provided. In step 706, a central input device accessible by the individual may be provided. In step 708, a peripheral input device accessible by the individual may be provided. The central display element, peripheral display element, central input device, and/or peripheral input device may comprise any of the examples previously described herein or any other device or system capable of displaying. Method 700 may perform central visual training and/or testing and peripheral visual training and/or testing contemporaneously in parallel method steps that may, but need not, occur simultaneously.

For the central visual training and/or testing, a central visual indicia possessing a visual trait may be displayed on a central display element in step 712. In step 714, inputs may be received using a central input device. The inputs received in step 714 may be defined relative to the traits potentially possessed by the central visual indicia displayed in step 712, such that each visual trait potentially possessed by a central visual indicia corresponds in a one-to-one ratio to the potential inputs that can be received in step 714. In step 716, the inputs received using the central input device may be compared to the traits possessed by the displayed central visual indicia, to determine whether the inputs correctly corresponded to the traits of the displayed central visual indicia.

Contemporaneous to the central visual training and/or testing steps, peripheral visual training and/or testing steps may be performed. In step 722, peripheral visual indicia possessing traits may be displayed on the peripheral display element. In step 724, inputs may be received using a peripheral input device. The inputs received in step 724 may correspond in a one-to-one fashion with the traits potentially possessed by the peripheral visual indicia displayed in step 722. In step 726, the inputs received may be compared to the traits possessed by the displayed peripheral visual indicia to determine whether the inputs correctly corresponded to the traits of the displayed indicia.

Method 700 may thereafter proceed to step 732 to output the result of the comparisons, either separately for central visual training and/or testing and peripheral visual training and/or testing, or in a combined fashion, or only one at a time. In step 734, the comparisons may be stored in a storage device such as a hard drive, flash memory, remote database, and the like. Step 734 may further store information describing the displayed visual indicia and/or information describing received inputs. For example, step 734 may store measurements of the speed of the responses of an individual, such as may be denoted from the time and indicia was displayed to the time at which the corresponding input was received. Other information, such as the properties of a displayed indicia, may also be stored in step 734.

Figure 8:
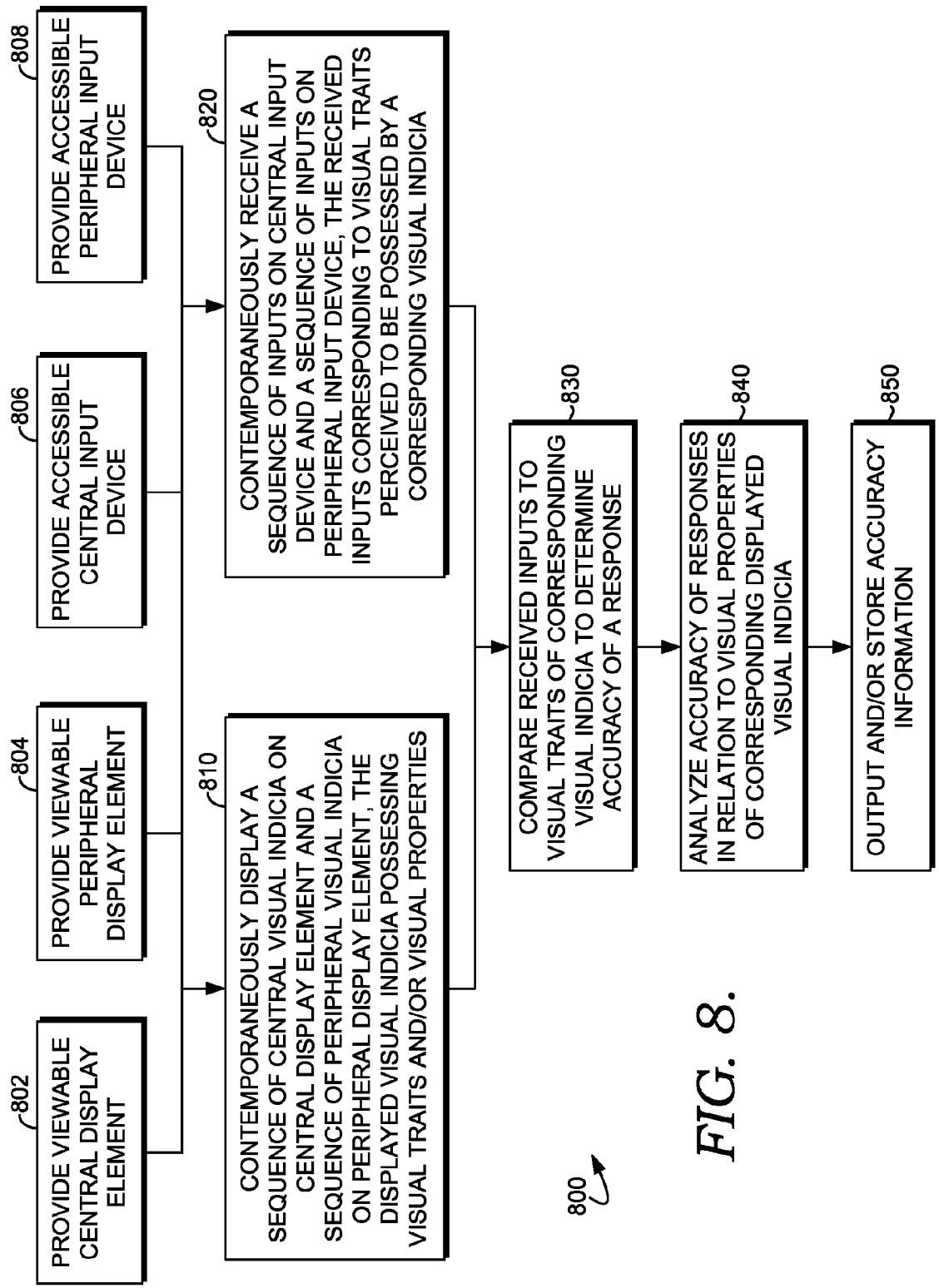
FIG. 8 illustrates a further method for training and/or testing the peripheral visual abilities of an individual.

Referring now to FIG. 8, a further method 800 for training and/or testing the peripheral visual abilities of an individual is illustrated. In step 802 a viewable central display element may be provided to an individual. In step 804 a viewable peripheral display element may be provided to an individual. In step 806 an accessible central input device may be provided to an individual. In step 808 an accessible peripheral input device may be provided to an individual.

In step 810, a sequence of central visual indicia may be displayed on a central display element while a sequence of peripheral visual indicia are contemporaneously displayed on a peripheral display element. In step 810, the displayed visual indicia may possess visual traits and/or properties. Occurring in parallel to step 810, step 820 may contemporaneously receive a sequence of inputs on a central input device any sequence of inputs on a peripheral input device. The inputs received in step 820 may correspond to visual traits perceived to be possessed by a corresponding visual indicia by the individual.

In step 830 the received inputs may be compared to the visual traits of the corresponding visual indicia to determine the accuracy of the responses of the individual. In step 840, the accuracy of the responses may be analyzed in relation to the visual properties of the corresponding displayed visual indicia. Step 840 may determine, for example, that the accuracy of the responses of an individual are reduced for indicia displayed on a particular quadrant of a display device, having a particular color, having a particular contrast with the background, displayed for a particular time duration, or the like. In step 850, the accuracy information, optionally in conjunction with the analysis performed at step 840, may be output and/or stored in an appropriate storage device.

Figure 9:
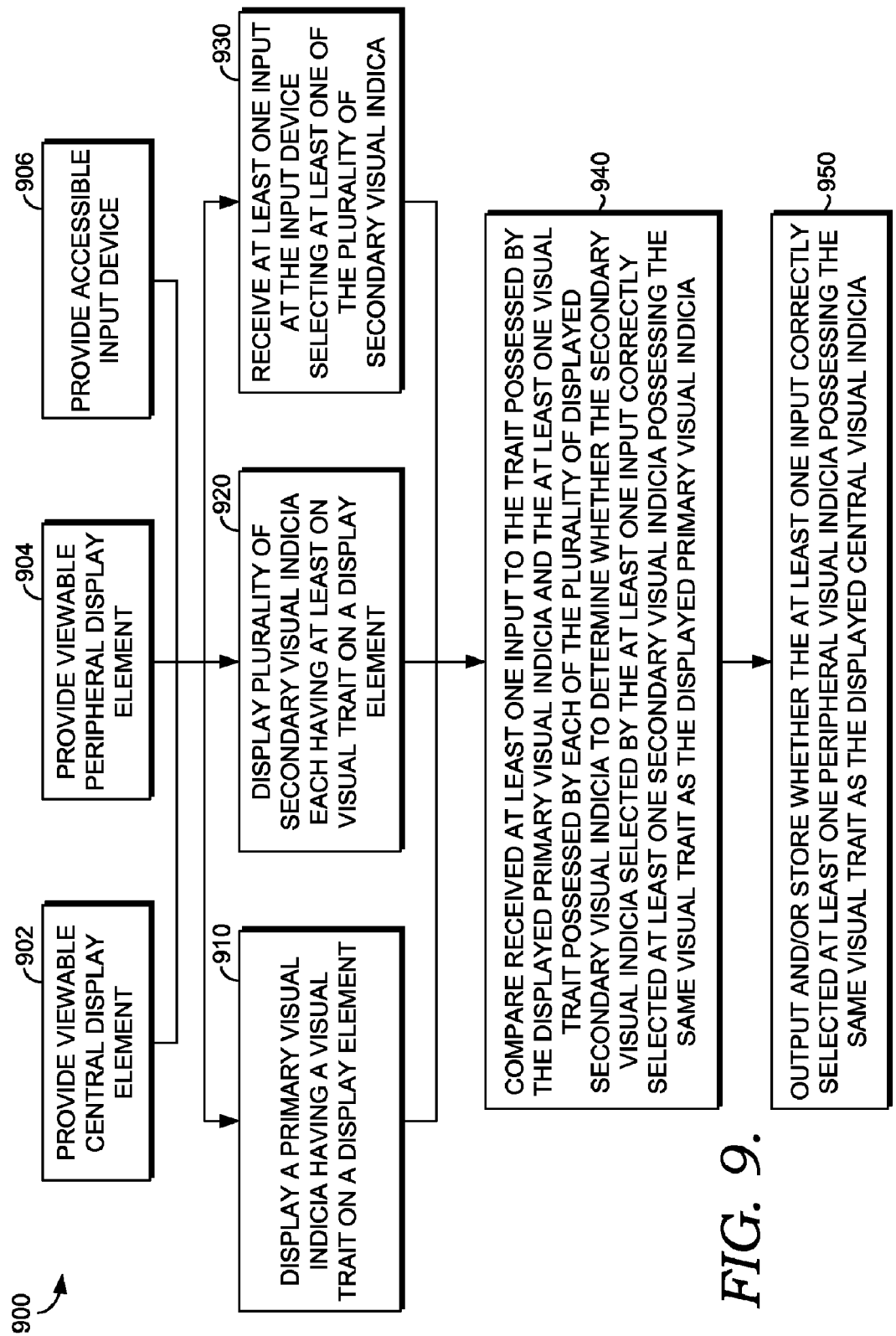
FIG. 9 illustrates a further method for training and/or testing the peripheral visual abilities of an individual.

Referring now to FIG. 9, a further method for training and/or testing the peripheral visual abilities of an individual is illustrated. In step 902, a viewable central display element may be provided to an individual. In step 904, a viewable peripheral element may be provided to an individual. In step 906, an accessible input device may be provided to the individual. The input device provided in step 906 may be either a central input device or a peripheral input device. The input device provided in step 906 may be used by an individual to select matching visual indicia, such as was described in conjunction with FIG. 5 above for the example where peripheral visual indicia may be selected that match a central visual indicia. However, systems and methods in accordance with the present invention may train and/or test the ability of an individual to identify central visual indicia that correspond to a displayed peripheral visual indicia.

As illustrated in the example of FIG. 9 for method 900, three steps may occur roughly simultaneously. In step 910, a primary visual indicia having a visual trait may be displayed on the primary display element. In step 920, a plurality of secondary visual indicia each having at least one visual trait may be displayed on a secondary visual display element. The plurality of secondary visual indicia displayed on the secondary display element may be displayed at different times or simultaneously. If method 900 is training and/or testing the ability of an individual to identify central visual indicia that correspond and match a peripheral visual indicia, step 910 may display a peripheral visual indicia, while step 920 may display a plurality of central visual indicia. However, step 910 may display a central visual indicia, while step 920 may display a plurality of peripheral visual indicia, which may use a system such as the example illustrated in FIG. 5. In step 930, at least one input may be received at the secondary input device selecting at least one of the plurality of secondary visual indicia that the individual perceives as matching the displayed primary visual indicia from step 910. Step 930 may be performed, for example, using a touch-sensitive screen.

Method 900 may thereafter proceed to step 940. Step 940 may compare the received at least one input to the trait possessed by the displayed primary visual indicia and the at least one visual trait possessed by each of the plurality of displayed secondary visual indicia to determine whether the selected secondary visual indicia correctly matches the trait possessed by the displayed primary visual indicia. Method 950 may then proceed to step 950, to output and/or store whether the at least one input correctly selected the matching visual indicia.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A system for training and/or testing the peripheral visual abilities of an individual, the system comprising:
    a central visual display element that presents a central visual indicia to the individual;
    at least one peripheral visual display element that presents peripheral visual indicia to the individual;
    at least one input device that receives inputs from the individual, the inputs being made in response to the displayed central visual indicia and the displayed peripheral visual indicia; and
    a control unit operably connected to the central visual display element, the peripheral display element, and the input device, the control unit operable to control the display of central visual indicia and the display of peripheral visual indicia, the control unit further operable to receive inputs from the at least one input device and determine whether the received inputs correctly correspond to the displayed central visual indicia and the displayed peripheral visual indicia.

2. The system of claim 1, wherein the central display element comprises a center portion of a display device and the peripheral display element comprises the outer portion of the display device.

3. The system of claim 1, wherein the at least one input device comprises:
    a central input device; and
    a peripheral input device.

4. The system of claim 3, wherein the peripheral input device and the peripheral display device comprise a touch sensitive display device.

5. The system of claim 4, wherein the central input device comprises a voice recognition system.

6. The system of claim 3, wherein the central input device and the central display element comprise a multi-touch device.

7. The system of claim 3, wherein the central display element comprises a center portion of a touch sensitive display device, the peripheral display element comprises an outer portion of the touch sensitive display device, and the peripheral input device comprises the touch sensitive display device.

8. The system of claim 7, wherein the central input device comprises a voice recognition system.

9. A method for training the peripheral visual abilities of an individual, the method comprising:
    providing the individual with a central display element adapted to display central visual indicia within the central field of view of the individual, each displayed central visual indicia possessing one of a plurality of traits;
    providing the individual with a peripheral display element adapted to display peripheral visual indicia within the peripheral field of view of the individual, each displayed peripheral indicia possessing one of a plurality of traits;
    providing the individual with a central input device adapted to receive any of a plurality of possible central inputs from the individual in response to traits possessed by the central visual indicia displayed by the central display element, each of the plurality of traits of the central visual indicia corresponding to one of the plurality of possible central inputs;
    providing the individual with a peripheral input device adapted to receive any of a plurality of possible central inputs from the individual in response to traits possessed by the peripheral visual indicia displayed by the peripheral display element, each of the plurality of traits of the peripheral visual indicia corresponding to one of the plurality of possible peripheral inputs;
    contemporaneously displaying a sequence of central visual indicia on the central display element and a sequence of peripheral visual indicia on the peripheral display element, each of the displayed central visual indicia and the displayed peripheral visual indicia possessing a visual trait;
    contemporaneously receiving inputs from the individual on the central input device and the peripheral input device;
    determining whether each of the inputs received by the central input device corresponds to the visual trait possessed by the central visual indicia displayed by the central display element when each input was received by the central input device;
    determining whether each of the inputs received by the peripheral input device corresponds to the visual trait possessed by the peripheral visual indicia displayed by the peripheral display element when each input was received by the peripheral input device;
    calculating a score based upon the number of received central inputs determined to correspond to the visual trait possessed by the central visual indicia displayed by the central display element when the input was received by the central input device and the number of received peripheral inputs determined to correspond to the visual trait possessed by the peripheral visual indicia displayed by the peripheral display element when the input was received by the peripheral input device; and
    outputting the calculated score.

10. The method of claim 9, wherein providing the individual with a central display element and providing the individual with a peripheral display element comprise providing the individual with a single display device such that a center portion of the single display element comprises the central display element and an outer portion of the single display device comprises the peripheral display element.

11. The method of claim 10, wherein the single display device provided comprises a touch sensitive display, and wherein providing a peripheral input device comprises providing the touch sensitive display.

12. The method of claim 11, wherein:
    displaying peripheral visual indicia possessing a visual trait comprises displaying visual indicia having a spatial location on the outer portion of the touch sensitive display device;
    receiving inputs from the individual on the peripheral input device comprises receiving touch inputs on the touch sensitive display device; and
    determining whether each of the inputs received on the peripheral input device corresponds to the visual trait possessed by the peripheral visual indicia displayed by the peripheral display element when each input was received by the peripheral input device comprises determining the distance between received touch inputs and the spatial location of displayed peripheral visual indicia.

13. The method of claim 12, wherein:
displaying central visual indicia possessing a visual trait comprises displaying a visual indicia possessing a visual trait that may be verbally identified;
receiving inputs from the individual on the central input device comprises receiving verbal responses from the individual on a speech recognition system; and
determining whether each of the inputs received on the central input device corresponds to the visual trait possessed by the central visual indicia displayed by the central display element when each input was received by the central display element comprises determining whether the verbal response received by the voice recognition system matches the visual trait possessed by the displayed central visual indicia.

14. The method of claim 13, wherein the displayed central visual indicia comprise Landolt Cs possessing a directional orientation.

15. The method of claim 9, wherein providing a central display element and providing a central input device comprise providing a multi-touch device.

16. The method of claim 15, wherein:
displaying central visual indicia possessing traits comprises displaying visual indicia having a directional orientation on the multi-touch device;
receiving inputs on a central input device comprises receiving directional touches on the multi-touch device; and
determining whether each of the inputs received by the central input device corresponds to the traits possessed by the central visual indicia comprises determining whether the received directional touches matches the directional orientation of the displayed central visual indicia.

17. The method of claim 16, wherein the displayed central visual indicia further comprise Landolt Cs having an orientation of up, down, left, or right.

18. A method of training and/or testing the visual abilities of an individual, the method comprising:
providing a primary display element viewable by the individual, the primary display element configured to display a primary visual indicia possessing one of a plurality of visual traits;
providing a secondary display element viewable by the individual, the secondary display element configured to display a plurality of secondary visual indicia possessing at least one of the plurality of visual traits;
providing an input device accessible to the individual, the input device configured to receive an input from the individual selecting at least one displayed secondary visual indicia displayed by the secondary display element;
defining a first indicia type, the first indicia type being a primary visual indicia having a trait selected from primary visual indicia displayed on the primary display element;
displaying a primary visual indicia having a first visual trait of the plurality of visual traits;
displaying a plurality of secondary visual indicia, each of the plurality of secondary visual indicia each having one of the plurality of traits, at least one of the plurality of secondary indicia having the first visual trait also possessed by the primary visual indicia;
receiving at least one input from the input device; and
comparing the received at least one input to the trait possessed by the displayed primary visual indicia and to the plurality of secondary visual indicia and the visual trait each of the secondary visual indicia possessed to determine whether the at least one input corresponds to the at least one of the secondary visual indicia having the first visual trait also possessed by the primary visual indicia.

* * * * *